United States Patent [19]

Siren

[11] Patent Number: 5,019,566
[45] Date of Patent: May 28, 1991

[54] METHOD OF TREATING INFLAMMATION WITH INOSITOL TRIPHOSPHATE

[75] Inventor: Matti Siren, Montagnola/Lugano, Switzerland

[73] Assignee: Perstorp AB, Perstorp, Sweden

[21] Appl. No.: 173,985

[22] Filed: Mar. 28, 1988

Related U.S. Application Data

[63] Continuation-in-part of Ser. No. 38,230, Apr. 14, 1987, abandoned, which is a continuation-in-part of Ser. No. 15,679, Feb. 17, 1987, Pat. No. 4,792,390, which is a continuation-in-part of Ser. No. 788,801 Oct. 18, 1985, Pat. No. 4,735,936.

[30] Foreign Application Priority Data

Apr. 16, 1986 [SE] Sweden .................... 8601709-2

[51] Int. Cl.$^5$ ............. A01N 57/00; A01N 37/08; A01N 31/08; C12N 9/96
[52] U.S. Cl. ................... 514/103; 514/573; 514/734; 514/738; 514/886; 435/155; 558/155
[58] Field of Search ........... 514/734, 886, 738, 573, 514/103

[56] References Cited

U.S. PATENT DOCUMENTS 2,723,938 11/1955 Buckwalter et al. ............ 514/103
3,591,665 7/1971 Kimura et al. ............. 252/400.2 XR

OTHER PUBLICATIONS

Lim et al., Biochim. Biophys. Acta 302, 316–328 (1973).
Tomlinson et al., Biochemistry, 1, No. 1, 166–171 (1962).
Kerr et al., Arch of Biochem & Biophys. 96, 347–352 (1962).
Suematsu et al., Biochem. & Biophys. Res. Comm., 120, No. 2, 481–485 (1984).
Desjobert, Bull. Ste. Chim. Biol., 36, No. 9; 1293–1299, (1954).
Streb et al., Nature, 306, 67–68 (1983).
Irvine et al., Biochem. J, 223, 237–243., (1984).

*Primary Examiner*—Shep K. Rose
*Assistant Examiner*—Theodore J. Criares
*Attorney, Agent, or Firm*—Scully, Scott, Murphy & Presser

[57] ABSTRACT

A method of reducing the negative effect of cadmium or aluminum ion or free-radicals in body tissues and a method of preventing or alleviating certain diseases and conditions by administering to a human or an animal a pharmaceutical composition comprising an amount of at least one specific isomer of inositol triphosphate sufficient to obtain said prevention or alleviation.

2 Claims, No Drawings

METHOD OF TREATING INFLAMMATION WITH INOSITOL TRIPHOSPHATE

CROSS-REFERENCE TO RELATED APPLICATIONS

This is a continuation-in-part of U.S. patent application, Ser. No. 038,230 filed Apr. 14, 1987, which is a continuation-in-part of U.S. patent application, Ser. No. 015,679 filed Feb. 17, 1987, now U.S. Pat. No. 4,797,390 which is a continuation-in-part of U.S. patent application, Ser. No. 788,801 filed Oct. 18, 1985, now U.S. Pat. No. 4,735,936.

FIELD OF THE INVENTION

The present invention relates to a method of preventing or alleviating different conditions in the body by administering thereto a pharmaceutical composition comprising inositol triphosphate.

BACKGROUND OF THE INVENTION

Even as early as the year 1900, different researchers had reported the finding of the organic phosphate compound phytic acid, i.e., 1,2,3,4,5,6-myo-inositol-hexakis(dihydrogenphosphate) (also sometimes called inositolhexaphosphoric acid) in plants. The content of phytic acid in different plants varies considerably. The content in grain is usually approximately 0.5–2%, with certain exceptions. Polished rice has a level of only 0.1% while wild rice contains as much as 2.2% phytic acid. Beans contain about 0.4–2%, oil plants approximately 2–5% and pollen 0.3–2%. The content of phytic acid in the plant varies during the growth period. The content is also influenced by, among other things, the climate.

In the literature there are reports of the presence of inositol pentaphosphate ($IP_5$) and inositol tetraphosphate ($IP_4$) in a few plants It is further known that phosphate derivatives lower than $IP_6$ are formed at germination of grain. For instance, the final products at germination are inositol and phosphate. The use of $IP_6$ has been described in several scientific publications. The majority of the authors of these articles have observed several negative effects on humans and animals when consuming $IP_6$ or substances containing $IP_6$. Feeding dogs with too high an amount of $IP_6$ gives rise for example to rachitis. In humans lack of zinc and as a consequence thereof slower growth of children has been observed. Anemia has been observed mainly in women. Because of the above mentioned negative effects on the mineral balance in human and animals, attempts have so far been made to reduce the intake of $IP_6$ and its derivatives to a minimum.

From C.A. Vol. 33 (1939), Abstr. No. 7351, No. ¾ the use phosphates including inositol phosphates as an antirachitic diet has been reported. No reference is made to specific inositol phosphates and nothing has been said in regard to complexing of metals.

U.S. Pat. No. 4,473,563 discloses the extra corporal treatment of erythrocytes to incorporate therein inositol phosphates to improve the oxygen supply. Then erythrocytes are separated from drawn blood which has been pumped out of the body for that purpose. After complicated treatment of erythrocytes the latter are re-introduced into the blood. There is no disclosure of administering inositol phosphates directly to the body. Moreover, nothing has been said in regard to reduction of the negative effect of cadmium or aluminum in the body or the inhibition or reduction of the formation of free-radicals or preventing or alleviating different conditions in the body by administering inositol phosphate.

In U.S. Pat. No. 2,723,938 the use of inositol phosphates is disclosed for stabilizing dispersions of an aqueous suspension of penicillin. This ensures that brief simple manual shaking will restore a state of complete and uniform dispersion of the penicillin after prolonged storage.

Cadmium has been found to be detrimental to human health and results from a large number of animal experiments obtained over many years show negative effects even at very low levels of cadmium. This would mean that a large proportion of the population is negatively affected, and this is above all valid for smokers. Epidemiological research shows a connection between the presence of cancer, high blood pressure and cardiovascular diseases (for instance, arteriosclerosis, heart infarction, sudden cardiac death) and the occurence of cadmium in the environment. Exposure to cadmium also seems to be a factor in increasing the risk of age diabetes.

In spite of very intensive research effort for many years seeking to prevent the above mentioned negative effects of cadmium and/or to prevent or alleviate the above mentioned problems created by cadmium, which in many cases involve very serious diseases, no good remedy without side effects has till now been found.

Aluminum has recently been recognized as a health hazard. In dialysis patients, aluminum causes dementia and osteomalicia. It is suspected that aluminum may cause many abnormalities, such as Alzheimers disease in humans. There are also investigations showing that aluminum can cause several diseases in animals. Aluminum can also increase lipid peroxidation in biological membranes, probably by destabilizing membrane structure. As for cadmium, no good remedy for Al-related diseases, without side effects has till now been found. Free-radicals have been suggested to be involved in the pathology of a number of diseases, such as autoimmune diseases and inflammatory diseases.

SUMMARY OF THE INVENTION

According to the present invention it has quite unexpectedly been found possible to reduce the above mentioned negative effects of cadmium, aluminum and freeradicals on humans and animals and thus to prevent or alleviate the connected diseases. Thus, a method of reducing the negative effect of cadmium or aluminum ion or free-radicals in body tissues has been brought about. At said method a pharmaceutical composition comprising an amount of at least one specific isomer of inositol triphosphate sufficient to interfere with cadmium or aluminum ion or inhibit or reduce the formation of free-radicals in the body is administered to a human or an animal.

In addition the present invention relates to a method of preventing or alleviating some diseases which may or may not be connected to cadmium, aluminum or freeradicals by administering to a human or an animal a pharmaceutical composition comprising an amount of at least one specific isomer of inositol triphosphate sufficient to obtain said prevention or alleviation.

The invention also covers a method of facilitating a transplant and a method of regulating unnormal levels of metal ions in a human or an animal.

DETAILED DESCRIPTION OF PREFERRED EMBODIMENTS

As examples of the diseases which the method according to the invention is useful to prevent or alleviate, there are mentioned eye diseases such as retinitis pigmentosa or damage of different parts of the eye such as the lens, a lung disease such as bronchitis, emphysema or lung fibrosis, an inflammatory condition such as arthritis, high blood pressure, cardiovascular diseases such as artherosclerosis or increase of platelet aggregation, diabetes, cell proliferation changes, damage to the central nervous system, a thrombotic condition such as damage to the endothelium, increase of platelet aggregation or inhibition of the prostacycline production, a hyperlipidaemic condition such as increased cholesterol levels, a light induced disease such as skin damages. It is believed that at least some of the above diseases are caused or aggravated by the presence of cadmium, aluminum or free-radicals, but the invention is not limited by said theory, since the method according to the invention is useful against said diseases whatever reason behind them.

The method according to the invention is also intended to facilitate or improve transplant of different organs and to regulate unnormal levels of metal ions in the body.

For production of the isomer or isomers of $IP_3$ which accomplish the above objectives and which is present in the composition used in the method according to the invention, one or more of the compounds $IP_6$, $IP_5$ or $IP_4$ or a natural product containing at least one of these compounds can be used as a starting material. In the cases where the starting material is a natural product, one with a content of at least 0.3%, preferably at least 1% of inositol phosphate ($IP_6 + IP_5 + IP_4$) is preferably chosen. Particularly suitable products are beans, bran, pollen and oil plants.

The $IP_3$ isomers present in the composition used according to the invention can, for example, be produced by enzymatic breakdown starting from $IP_4$, $IP_5$ and/or $IP_6$.

According to the invention a procedure where the above mentioned higher inositol phosphates $IP_6$, $IP_5$ and/or $IP_4$ are broken down enzymatically to $IP_3$ with phytase enzyme, for instance, is preferred. Phytase enzyme is normally present in all inositol phosphate-containing plants and seeds. Because of this it is, according to the invention, usually not necessary to add the enzyme if a natural product is used as starting material. In the cases where the natural product has too low an enzymatic activity or when $IP_6$, $IP_5$ or $IP_4$ or a mixture of these is used as starting material, a phytase enzyme, for example, from bran is added.

A suitable way to treat the natural or crude starting material is to pretreat it, for instance by breakage or removal of outer membrane and removal of unwanted constituents. Thus, when using pollen the allergens should be removed. Thereafter, the material is soaked in water to make the inositol phosphate available for breaking down and to activate the enzyme. In the cases where an extra quantity of enzymes is necessary, this quantity is added at this stage. The enzyme is then allowed to act for so long a time as is necessary for the intended degree of hydrolysis to be achieved.

The hydrolysis takes place at a suitable temperature, usually 20–70° C., preferably 30–40° C. and at optimal pH-level for the phytase present. In order to stop the hydrolysis at the intended level the enzyme may be destroyed or inactivated, for instance by a rapid heating of the hydrolysed starting material. This also ensures that an uncontrolled and undesired continued hydrolysis of $IP_3$ in the stomach will not continue when the composition is administered. In order to transfer the material to a form which is stable at storage it can suitably be freeze dried. Yeast can be used advantageously as a source of phytase. Preferably baker's yeast is used. When using Yeast essentially only one isomer of $IP_3$ is obtained, namely D-myo-inositol-1,2,6-triphosphate.

The above mentioned procedure, in applicable parts with possible modifications, can be used also when one or more of the compounds $IP_6$, $IP_5$ or $IP_4$ per se are used as starting material.

The pharmaceutical composition used in the method according to the invention comprises as a pharmaceutically active ingredient at least one specific isomer of inositol triphosphate ($IP_3$).

It is suitable that the composition used according to the invention exists in unit dosage form. Tablets, granulates or capsules are suitable administration forms for such unit dosage. Furthermore, tablets and granulates can easily be surface treated such as to provide an enteric coating to prevent an uncontrolled hydrolysis in the stomach and to bring about a desired absorption in the intestine. Other suitable administration forms are slow release and transdermal administration. A usual pharmacetically acceptable additive, excipient and/or carrier can be included in the composition. The tablets or granulates can also contain a disintegrant which causes the tablets or the granulates, respectively, to disintegrate easily in the intestine. In certain cases, especially in acute situations, it is preferable to use the unit dosage in the form of a solution for intravenous administration.

The pharmaceutical composition can also consist as such of $IP_3$ solely without any additive, excipient or carrier.

If desired, the composition can be free of other inositol phosphates $IP_1$, $IP_2$, $IP_4$, $IP_5$ and $IP_6$ Accordingly, the mixture of $IP_3$ isomers can have a purity of 90–100%, such as 93–100% or preferably 95–100%.

Alternatively, the pharmaceutical composition used in the method can consist of or comprise one or more specific $IP_3$ isomers disclosed hereinafter, each present in substantiallY pure form. Thus, the different isomers can be isolated from each other in substantially pure form, which means that they have a purity of 80–100%, such as 82–100% or 85–100%, preferably 90–100%. Since the isomers can be produced in pure form they can be mixed in any proportion, of course.

The production of $IP_3$ and the isolation of the different isomers thereof are disclosed in the co-pending U.S. patent application Ser. No. 788,829.

It is in most cases suitable that the $IP_3$-isomer or isomers in the composition used in the method according to the invention is present in salt form in order not to affect the mineral balance negatively. The salt should preferably consist of a sodium, calcium, zinc or magnesium salt or a mixture of two or more of these salts. Calcium and zinc salts or mixtures of these are especially preferred. The isomer of $IP_3$ can also partly be present as a salt of one or more physiologically acceptable compounds in the lanthanide series.

For the above mentioned reasons it is also an advantage if the composition contains a surplus or an extra addition of at least one pharmaceutically acceptable salt of calcium, zinc, magnesium or copper with a mineral acid or organic acid. This is especially valuable for older persons who are often deficient in these minerals.

The composition used according to the present invention can preferably also contain at least one substance containing selenium, an unsaturated fatty acid, such as gamma linoleic acid, vitamin E, vitamin C or a pharmaceutically acceptable organic acid or salt thereof, such as citrate, oxalate, malonate and tartrate. These substances also help to counteract the negative effect of cadmium, aluminum and the formation of free-radicals in the body and/or to give in addition thereto, in certain cases, a desirable effect together with the IP$_3$ isomer in the composition. The content of selenium in the composition is preferably such that the daily intake is about 0.7-8 ug/kg body weight preferablY 0.7-3.3 ug. For vitamin E the corresponding values are about 0.1-2 mg and 0.1-1 mg, respectively.

The composition is suitably free from penicillin.

For administration to human patients appropriate dosages can routinely be determined by those skilled in this art by extension of the results obtained in animals at various dosages. The preferred dosage for humans falls within the range of 0.1 to 100, especially 0.1-50 mg IP$_3$/day/kg body weight.

In animal experiments, no toxic effects were seen after administration of very high doses of IP$_3$, 160mg/kg body weight by intravenous injection to mice or 1600 mg/kg body weight by intraperitoneal injection to mice.

The composition used according to the present invention contains at least one, sometimes two or more of the following substances, which correspond to the essential IP$_3$-isomer or isomers mentioned above:

D-myo-inositol-1,2,6-triphosphate of the formula

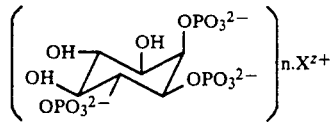

where X is hydrogen, at least one univalent, divalent or multivalent cation, or a mixture thereof, n is the number of ions, and z is the charge of the respectively ion;

D-myo-inositol-1,2,5-triphosphate of the formula

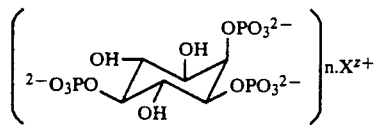

where X, n and z have the above mentioned meaning; myo-inositol-1,2,3.-triphosphate of the formula

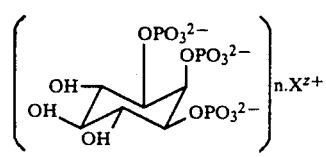

where X, n and z have the above mentioned meaning; L-myo-inositol-1,3,4-triphosphate of the formula

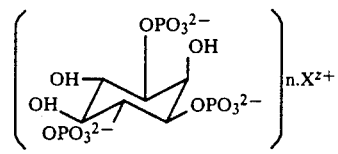

where X, n and z have the above mentioned meaning.

In each of the above formulas n ranges between 6 to 1 inclusive and z ranges from 1 to 6 inclusive. Preferably, n is between 3 to 6 inclusive and z is 3, 2 or 1. Of above isomers D-myo-inositol-1,2,6-triphosphate is preferred.

Other inositol triphosphate isomers that may be utilized in the present invention as the active IP$_3$ ingredient in the composition have the structural formula

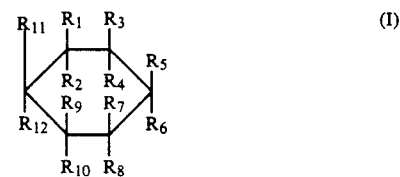

One group of inositol triphosphate compounds is defined by structural formula (I) where three of $R_1$, $R_3$, $R_5$, $R_7$, $R_{10}$ and $R_{11}$ are hydroxyl and the remaining three are phosphate and $R_2$, $R_4$, $R_6$, $R_8$, $R_9$ and $R_{12}$ are hydrogen.

Another group of inositol triphosphates is defined by structural formula (I) where three of $R_1$, $R_3$, $R_6$, $R_7$, $R_9$ and $R_{12}$ are hydroxyl and the remaining three are phosphate and $R_2$, $R_4$, $R_5$, $R_8$, $R_{10}$ and $R_{11}$ are hydrogen.

Still another group of inositol triphosphates is defined by structural formula (I) where three of $R_1$, $R_3$, $R_5$, $R_8$, $R_{10}$ and $R_{12}$ are hydroxyl and the remaining three are phosphate and $R_2$, $R_4$, $R_6$, $R_7$, $R_9$ and $R_{11}$ are hydrogen.

Yet another group of inositol triphosphates is defined by structural formula (I) where three of $R_1$, $R_4$, $R_5$, $R_8$, $R_9$ and $R_{12}$ are hydroxyl and the remaining three are phosphate and $R_2$, $R_3$, $R_6$, $R_7$, $R_{10}$ and $R_{11}$ are hydrogen.

Still yet another group of inositol triphosphates is defined by structural formula (I) where three of $R_1$, $R_3$, $R_6$, $R_8$, $R_9$ and $R_{12}$ are hydroxyl and the remaining three are phosphate and $R_2$, $R_4$, $R_5$, $R_7$, $R_{10}$ and $R_{11}$ are hydrogen.

Even still another group of inositol triphosphates is defined by structural formula (I) where three of $R_1$, $R_3$, $R_6$, $R_7$, $R_{10}$ and $R_{12}$ are hydroxyl and the remaining three are phosphate and $R_2$, $R_4$, $R_5$, $R_8$, $R_9$ and $R_{11}$ are hydrogen.

Even yet group of inositol triphosphates is defined by structural formula (I) where three of $R_1$, $R_3$, $R_5$, $R_8$, $R_{10}$ and $R_{11}$ are hydroxyl and the remaining three are phosphate and $R_2$, Finally, another group of inositol triphosphates is defined by structural formula (I) where three of $R_1$, $R_3$, $R_5$, $R_7$, $R_9$ and $R_{11}$ are hydroxyl and the remaining three are phosphate and $R_2$, $R_4$, $R_6$, $R_8$, $R_{10}$ and $R_{12}$ are hydrogen.

Particular inositol triphosphate compounds within the contemplation of the above formula include compounds having the structural formula (I) where $R_5$, $R_7$ and $R_{10}$ are phosphate, $R_1$, $R_3$ and $R_{11}$ are hydroxyl and $R_2$, $R_4$, $R_6$, $R_8$, $R_9$ and $R_{12}$ are hydrogen;

$R_1$, $R_{10}$ and $R_{11}$ are phosphate, $R_3$, $R_5$ and $R_7$ are hydroxyl and $R_2$, $R_4$, $R_6$, $R_8$, $R_9$ and $R_{12}$ are hydrogen;

$R_1$, $R_3$ and $R_{11}$ are phosphate, $R_5$, $R_7$ and $R_{10}$ are hydroxyl and $R_2$, $R_4$, $R_6$, $R_8$, $R_9$ and $R_{12}$ are hydrogen;

$R_3$, $R_5$ and $R_7$ are phosphate, $R_1$, $R_{10}$ and $R_{11}$ are hydroxyl and $R_2$, $R_4$, $R_6$, $R_8$, $R_9$ and $R_{12}$ are hydrogen;

$R_3$, $R_7$ and $R_{10}$ are phosphate, $R_1$, $R_5$ and $R_{11}$ are hydroxyl and $R_2$, $R_4$, $R_6$, $R_8$, $R_9$ and $R_{12}$ are hydrogen;

$R_3$, $R_{10}$ and $R_{11}$ are phosphate, $R_1$, $R_5$ and $R_7$ are hydroxyl and $R_2$, $R_4$, $R_6$, $R_8$, $R_9$ and $R_{12}$ are hydrogen;

$R_1$, $R_3$ and $R_6$ are phosphate, $R_7$, $R_9$ and $R_{12}$ are hydroxyl and $R_2$, $R_4$, $R_5$, $R_8$, $R_{10}$ and $R_{11}$ are hydrogen;

$R_6$, $R_7$ and $R_9$ are phosphate, $R_1$, $R_3$ and $R_{12}$ are hydroxyl and $R_2$, $R_4$, $R_5$, $R_8$, $R_{10}$ and $R_{11}$ are hydrogen;

$R_3$, $R_5$ and $R_8$ are phosphate, $R_1$, $R_{10}$ and $R_{12}$ are hydroxyl and $R_2$, $R_4$, $R_6$, $R_7$, $R_9$ and $R_{11}$ are hydrogen;

$R_1$, $R_3$ and $R_{12}$ are phosphate, $R_5$, $R_8$ and $R_{10}$ are hydroxyl and $R_2$, $R_4$, $R_6$, $R_7$, $R_9$ and $R_{11}$ are hydrogen;

$R_1$, $R_3$ and $R_5$ are phosphate, $R_8$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_8$ are phosphate, $R_3$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_{12}$ are phosphate, $R_3$, $R_8$ and $R_{10}$ are hydroxyl and $R_2$, $R_4$, $R_6$, $R_7$, $R_9$ and $R_{11}$ are hydrogen;

$R_1$, $R_3$ and $R_{12}$ are phosphate, $R_6$, $R_8$ and $R_9$ are hydroxyl and $R_2$, $R_4$, $R_5$, $R_7$, $R_{10}$ and $R_{11}$ are hydrogen;

$R_1$, $R_3$ and $R_6$ are phosphate, $R_7$, $R_{10}$ and $R_{12}$ are hydroxyl and $R_2$, $R_4$, $R_5$, $R_8$, $R_9$ and $R_{11}$ are hydrogen;

$R_4$, $R_5$ and $R_8$ are phosphate, $R_1$, $R_9$ and $R_{12}$ are hydroxyl and $R_2$, $R_3$, $R_6$, $R_7$, $R_{10}$ and $R_{11}$ are hydrogen;

$R_3$, $R_5$ and $R_8$ are phosphate, $R_1$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_8$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_7$, $R_9$ and $R_{11}$ are hydroxyl and $R_2$, $R_4$, $R_6$, $R_8$, $R_{10}$ and $R_{12}$ are hydrogen;

$R_1$, $R_3$ and $R_{12}$ are phosphate, $R_5$, $R_8$ and $R_9$ are hydroxyl and $R_2$, $R_4$, $R_6$, $R_7$, $R_{10}$ and $R_{11}$ are hydrogen;

$R_1$, $R_3$ and $R_8$ are phosphate, $R_5$, $R_9$ and $R_{12}$ are hydroxyl and $R_2$, $R_4$, $R_6$, $R_7$, $R_{10}$ and $R_{11}$ are hydrogen;

$R_3$, $R_5$ and $R_{12}$ are phosphate, $R_1$, $R_8$ and $R_9$ are hydroxyl and $R_2$, $R_4$, $R_6$, $R_7$, $R_{10}$ and $R_{11}$ are hydrogen;

$R_1$, $R_5$ and $R_9$ are phosphate, $R_3$, $R_8$ and $R_{12}$ are hydroxyl and $R_2$, $R_4$, $R_6$, $R_7$, $R_{10}$ and $R_{11}$ are hydrogen;

$R_1$, $R_5$ and $R_{12}$ are phosphate, $R_3$, $R_8$ and $R_9$ are hydroxyl and $R_2$, $R_4$, $R_6$, $R_7$, $R_{10}$ and $R_{11}$ are hydrogen;

$R_1$, $R_3$ and $R_9$ are phosphate, $R_5$, $R_8$ and $R_{12}$ are hydroxyl and $R_2$, $R_4$, $R_6$, $R_7$, $R_{10}$ and $R_{11}$ are hydrogen;

$R_5$, $R_9$ and $R_{12}$ are phosphate, $R_1$, $R_3$ and $R_8$ are hydroxyl and $R_2$, $R_4$, $R_6$, $R_7$, $R_{10}$ and $R_{11}$ are hydrogen;

$R_1$, $R_8$ and $R_9$ are phosphate, $R_3$, $R_5$ and $R_{12}$ are hydroxyl and $R_2$, $R_4$, $R_6$, $R_7$, $R_{10}$ and $R_{11}$ are hydrogen;

$R_1$, $R_8$ and $R_{12}$ are phosphate, $R_3$, $R_5$ and $R_9$ are hydroxyl and $R_2$, $R_4$, $R_6$, $R_7$, $R_{10}$ and $R_{11}$ are hydrogen;

$R_5$, $R_8$ and $R_{12}$ are phosphate, $R_1$, $R_3$ and $R_9$ are hydroxyl and $R_2$, $R_4$, $R_6$, $R_7$, $R_{10}$ and $R_{11}$ are hydrogen;

$R_1$, $R_9$ and $R_{12}$ are phosphate, $R_3$, $R_5$ and $R_8$ are hydroxyl and $R_2$, $R_4$, $R_6$, $R_7$, $R_{10}$ and $R_{11}$ are hydrogen;

$R_5$, $R_8$ and $R_9$ are phosphate, $R_1$, $R_3$ and $R_{12}$ are hydroxyl and $R_2$, $R_4$, $R_6$, $R_7$, $R_{10}$ and $R_{11}$ are hydrogen;

$R_3$, $R_8$ and $R_9$ are phosphate, $R_1$, $R_5$ and $R_{12}$ are hydroxyl and $R_2$, $R_4$, $R_6$, $R_7$, $R_{10}$ and $R_{11}$ are hydrogen;

$R_3$, $R_9$ and $R_{12}$ are phosphate, $R_1$, $R_5$ and $R_8$ are hydroxyl and $R_2$, $R_4$, $R_6$, $R_7$, $R_{10}$ and $R_{11}$ are hydrogen;

$R_3$, $R_8$ and $R_{12}$ are phosphate; $R_1$, $R_5$ and $R_9$ are hydroxyl and $R_2$, $R_4$, $R_6$, $R_7$, $R_{10}$ and $R_{11}$ are hydrogen; and $R_8$, $R_9$ and $R_{12}$ are phosphate, $R_1$, $R_3$ and $R_5$ are hydroxyl and $R_2$, $R_4$, $R_6$, $R_7$, $R_{10}$ and $R_{11}$ are hydrogen The above formula describes specific isomers of inositol triphosphate where the inositol is selected from the group myoinositol, cisinositol, epiinositol, alloinositol, neoinositol, mucoinositol, chiroinositol and scylloinositol.

$IP_3$ may be the sole pharmaceutically active ingredient in the composition used. However, also other pharmaceutically active ingredients can be present therein. The amount of $IP_3$ should then constitute 5 to 95 or 15 to 80, such as 25 to 60 per cent by weight of said active ingredients.

Moreover, the composition can be a multi-vitamin unit containing to 60, such as 2 to 40 or preferably 2 to 25 per cent by weight of $IP_3$ based on the total weight of pharmaceutically active ingredients.

The composition usually contains 0.01–1.5 g, such as 0.05–1.3 or preferably 0.1–1 g of $IP_3$.

The invention also comprises a method of preventing or alleviating one of the following conditions; damage to cell membranes, damage to the placenta, the prostate or the testicles, damage to the conducting system of the heart, migraine headache, menstruation disorders, kidney damage, an allergy or multiple sclerosis, and wherein said condition may or may not be attributable to, caused or aggravated by the presence of cadmium, aluminum or free-radicals in the body.

The method comprises administering to a human or an animal a pharmaceutical composition comprising an amount of at least one specific isomer of inositol triphosphate sufficient to obtain said prevention or alleviation.

Furthermore, the invention covers a method of alleviating the detrimental effect of radiation in the body, which method comprises administering to a human or an animal an amount of radiation. For instance, the radiation can be X-ray or nuclear radiation, but other kinds of radiation are also contemplated.

The invention is further explained below in connection with embodiment examples of which example 1 and 2 show that platelet aggregation can be counteracted by injection or oral administration of $IP_3$ Example 3 relates to the effect of $IP_3$ in changing the distribution of cadmium in different organs of mice. Example 4 shows that $IP_3$ prevents an increase of platelet aggregation in humans caused by smoking. In example 5 it is shown that an increased blood glucose level in mice can be counteracted by injection of $IP_3$. Examples 6 and 7 show that $IP_3$ prevents or reduces the formation of free-radicals. Example 8 illustrates experiments on binding constants between different metals and $IP_3$ Examples 9 and 10 teach production of $IP_3$ Example 11 shows the production of a solution of a potassium salt of $IP_3$ for injection and example 12 shows the production of tablets of the calcium salt of $IP_3$ Example 13 shows the reversal of platelet aggregtion by addition of $IP_3$. In example 14 it is shown how to reduce the formation of thrombus. Examples 15 and 16 illustrate the reduction of hypertension by addition of $IP_3$. Example 17 relates to the beneficial effect of $IP_3$ on lipid levels. In example 18 $IP_3$ is shown to reduce the occurence of artherosclerosis. Example 19 describes the reduction of inflammation by addition of $IP_3$. Example 20 teaches the protective effect of $IP_3$ against damage on transplanted organs. The iron binding effect of $IP_3$ is illustrated in example 21. Examples 22-25 show the production of different inositol triphosphate compounds.

Methods for examples 1 and 2

Rabbits (New Zealand white, males) weighing 2-2.5 kg were used. They were fed a diet free from inositol phosphates, for 10 days before the experiment.

Animal experimental procedure

In example 1 (intravenous injection of test-substances), the following procedure was used:

| Time: | Treatment |
|---|---|
| 0 minutes: | Intravenous injection of inositol phosphate in 1 ml physiological saline, or 1 ml physiological saline respectively. |
| 1 minute: | Blood sample 1 (9 ml + 1 ml 3.8% sodium citrate) taken. |
| 2 minutes: | Intravenous injection of 4 microgram Cd as $CdCl_2$ in 0.5 ml physiological saline, or 0.5 ml physiological saline respectively. |
| 5 minutes: | Blood sample 2 (9 ml + 1 ml 3.8% sodium citrate) taken. |

In example 2 (oral administration of test substances) the same procedure was used except that the first injection was replaced by oral administration of the inositol phosphates or saline respectively. Injection volumes were the same as those above. The oral dosing was made 1 hour before blood sample 1. The blood sampling and the second intravenous injection were made as above. The rabbits were unanesthetized during the experiments.

Treatment of samples

The two blood samples from each animal were centrifuged at 1200 revolutions per minute, for 10 minutes, and the plasma with platelets was obtained.

The plasma with platelets from the two samples was analyzed concerning the response to addition of ADP (adenosin diphosphate) in an aggregometer (Chronopar Corp Mod, 440) according to Born (J. Physiol: 67,1968). The two samples were analyzed simultaneously at the same concentration (1-20 micromolar) of ADP, in the two channels of the instrument.

The principle of this test is that the plasma with platelets is turbid, and has a low transmittance for light. As ADP is added, the platelets aggregate and form clumps. This results in an increase of transmittance which is quantified by the instrument. The response to ADP was measured in scale units, with 80 scale units representing maximal aggregation. In order to have a maximal sensitivity of the method to pick up changes in platelet reactivity, the ADP dose should cause a response of 5-30 scale units. This was normally achieved with 5 uM ADP, but in some animals a lower or higher dose (1-20 uM) was necessary.

The result of the test is expressed as maximal aggregation in sample 2 (scale units) minus maximal aggregation in sample 1.

An increase in platelet aggregation has been reported to occur after smoking, and in cardiovascular diseases, and agents which suppress platelet aggregation are believed to be of value in treating, for example, cardiovascular diseases.

Example 1

Methods were as above. Four different isomers of $IP_3$ were tested, the intravenously injected amount was $2 \times 10^{-7}$ mol. The isomers were D-myo-inositol-1,2,6-triphosphate (1,2,6), L-myo-inositol-1,3,4-triphoshate (1,3,4), myo-inositol-1,2,3-triphosphate (1,2,3) and D-myo-inositol-1,2,5-triphosphate (1,2,5).

The results were as follows:

| Injection 1 | Injection 2 | No | Change in aggregation from sample 1 to sample 2 (scale units) |
|---|---|---|---|
| 1,2,6 | Cd | 15 | −0.4 |
| 1,2,3 | Cd | 12 | +0.3 |
| 1,3,4 | Cd | 13 | +0.6 |
| 1,2,5 | Cd | 14 | +1.7 |
| Saline | Cd | 14 | +3.4 |

The results show that all the tested isomers had a good effect in preventing the cadmium-induced aggregation, and that the best effect was obtained with 1,2,6.

Example 2

The methods were as above. D-myo-inositol-1,2,6-triphosphate ($IP_3$), dose $2 \times 10^{-5}$ mol, was given orally.
The following results were obtained:

| Oral administration | Injection | No | Change in aggregation from sample 1 to sample 2 |
|---|---|---|---|
| Saline | Cd | 23 | +1.9 |
| $IP_3$ | Cd | 15 | −0.4 |

At the dose used in this experiment, IP3 prevented the effect of Cd on platelet aggregation.

Example 3

Mice weighing 18-20 gram at the start of the experiment were used. During the experiment and for at least the experiment the mice were fed a semisynthetic diet free of inositol phosphates. The mice were divided in two groups.

They received daily intraperitoneal injections of physiological saline or D-myo-inositol-1,2,6-triphosphate (IP3) for 9 days. The does of IP3 was $10^{-6}$ mol/day and the injected volume was 0.2 ml.

On day two of the experiment, 5-10 minutes after the second intraperitoneal injection, all mice received an intravenous injection of 2.5 microcurie of $^{109}$Cd as cadmium chloride in 50 ul of saline. After the last intraperitoneal injection the mice were killed and several organs were dissected out and weighed.

Radioactivity in the different organs was measured by counting with a gamma-counter. Radioactivity in the organs of the IP3-treated animals was compared with that of control animals, which had been treated with saline for the same period of time. In the results radioactivity in the organs of the animals treated with IP3 is expressed as % of the radioactivity found in controls. The results were as follows:

| Organ | Cd-level compared to control (%) |
|---|---|
| Lung | 74 |
| Heart | 67 |
| Aorta | 65 |
| Spleen | 57 |
| Salivary gland | 87 |
| Liver | 100 |
| Kidney | 104 |

These results show that IP3 causes a strong decrease in cadmium concentration in lung, aortic artery, heart and spleen. Liver and kidney levels were not affected.

Example 4

The effect of D-myo-inositol-1,2,6-triphosphate (IP3) on platelet aggregation after smoking in humans was studied.

Four young healthy male non-smokers received, on two occasions, a capsule containing 50 mg of IP3 or 50 mg of a placebo. Neither subject nor investigator knew whether the subject had received IP3 or placebo.

Two hours after ingestion of the capsule, a blood sample was obtained. The subject then smoked two cigarettes in rapid succession. A second blood sample was obtained after smoking. The aggregation responses of the platelets to ADP and collagen in the two samples were determined, using essentially the same procedure as in example 1. The results are expressed as change in aggregation from the pre-smoking to the post-smoking sample. A positive sign indicates that aggregation was stronger after smoking.

| Aggregating agent | Concentration of aggregating agent | IP3 | Placebo | Difference between IP3 and placebo |
|---|---|---|---|---|
| ADP | 0.5 mmol | +1.5 | +7.25 | 5.85 |
| " | 1 mmol | −1.5 | +0.25 | 1.75 |
| " | 2.5 mmol | −1.5 | 0 | 1.5 |
| " | 5 mmol | −2.5 | −0.75 | 1.75 |
| Collagen | 0.5 mg | +5.15 | +12.25 | 6.5 |
| " | 1 mg | −8.25 | +1.75 | 10.0 |
| " | 2.5 | −3.75 | 0 | 3.75 |
| " | 5 mg | −1.5 | −0.25 | 1.25 |

In the placebo group, smoking caused an increase in aggregation, which was most marked at low concentrations of aggregation agents. In all cases this effect was counteracted by IP3. Thus, IP3 prevents increase of platelet aggregation caused by smoking.

Example 5

Mice, 10 in each group, were injected intraperitoneally with the Na-salt of D-myo-inositol-1,2,6-triphosphate (IP3) in three dose levels or with physiological saline. 30 minutes after this injection, all mice except one control group received an intravenous injection of alloxan, 50 mg/kg in saline.

The animals were starved for 12 hours before, and one hour after the alloxan injection. 72 hours after the alloxan injection, a blood sample from the mice was analyzed with respect to glucose level. The results were as follows:

| Dose of IP3 mg/kg | Dose of alloxan mg/kg | Blood glucose |
|---|---|---|
| 0 | 0 | 216 |
| 0 | 50 | 864 |
| 800 | 50 | 857 |
| 1600 | 50 | 677 |

Alloxan causes diabetes and increased blood glucose level by promotion free-radical reactions in the insulin producing cells. With IP3 there was a dose-dependent decrease in blood glucose levels, and the highest dose gave some protection to the alloxan.

Example 6

Lipid peroxidation was studied in lipid micelles. The following reaction mixture was incubated for 2 hours at 37° C.:

| | |
|---|---|
| 0.4 ml | Clark-Lubs buffer pH 5.5 |
| 0.2 ml | phospholipid liposomes |
| 0.1 ml | IP3 0.5–5 mM or 0.1 ml H2O |
| 0.1 ml | Fe$^{2+}$ 1 mM or 0.1 ml H2O |
| 0.1 ml | Al$^{3+}$ 4 mM or 0.1 ml H2O |
| 0.1 ml | H2O |

The IP3 was D-myo-inositol-1,2,6-triphosphate. After incubation, 0.5 ml of Thiobarbituric acid +0.5 ml 25% HCl was added and the mixture was heated at 100° C. for 15 minutes. 1 ml Lubrol PX 1% (Sigma) was added and lipid peroxidation was measured by measuring absorbance at 532 nm. The results were as follows:

| Experiment | Concentration, mM | | | Absorbance 532 nm |
|---|---|---|---|---|
| | Fe$^{2+}$ | Al$^{3+}$ | IP3 | |
| 1 | 0.1 | 0 | 0 | 0.36 |
| 2 | 0 | 0.4 | 0 | 0.12 |
| 3 | 0.1 | 0.4 | 0 | 0.89 |
| 4 | 0.1 | 0.4 | 0.5 | 0.36 |
| 5 | 0.1 | 0 | 0.5 | 0.30 |
| 6 | 0.1 | 0 | 0.4 | 0.26 |

-continued

| Experiment | Concentration, mM | | | Absorbance 532 nm |
|---|---|---|---|---|
| | $Fe^{2+}$ | $Al^{3+}$ | $IP_3$ | |
| 7 | 0.1 | 0 | 0.2 | 0.29 |
| 8 | 0.1 | 0 | 0.1 | 0.28 |
| 9 | 0.1 | 0 | 0.05 | 0.27 |
| 10 | 0 | 0 | 0 | 0.13 |

$Fe^{2+}$ caused lipid peroxidation (group 1 vs 10). $Al^{3+}$ itself caused no peroxidation (2 vs 10) whereas the combination of $Fe^{2+}+Al^{3+}$ caused much stronger peroxidation than $Fe^{2+}$ alone (1 vs 3). Addition of $IP_3$ completely prevented the interaction between $Fe^{2+}$ and $Al^{3+}$ (3 vs 4). In systems with only $Fe^{2+}$, $IP_3$ caused marked reduction in radical formation (1 vs 5-9).

Example 7

Reaction mixtures with the following compositions were incubated for 5 minutes at 37° C.:

| | |
|---|---|
| $KH_2PO_4$ buffer pH 7.4 | 20 mM |
| EDTA | 0.1 mM |
| Salicylate | 1 mM |
| Ascorbate | 1 mM |
| $H_2O_2$ | 3.3 mM |
| $Fe^{3+}$ | 0.05 mM |
| $IP_3$ | 0, 2.5, 5 or 10 mM | the products formed by oxidation of salicylate were quantified with HPLC. The $IP_3$ was D-myo-inositol-1,2,6-triphosphate.

The system studies radical scavenging. Under these reaction conditions, all $Fe^{3+}$ will form complex with EDTA. The Fe-EDTA complex will induce free-radical formation, and the ability of $IP_3$ to prevent oxidation of salicylate is studied.

The results of the experiment were:

| Concentration of $IP_3$, mM | Relative amount of salicylate oxidized |
|---|---|
| 0 | 100 |
| 2.5 | 44 |
| 5 | 43 |
| 10 | 19 |

Thus, $IP_3$ able to act as a radical scavenger, thereby preventing free-radical induced damage to other molecules or tissues.

Example 8

The relative metal binding constants for D-myo-inositol-1,2,6-triphosphate ($IP_3$) and calcium, cadmium, aluminum and iron respectively were determined.

A solution consisting of 4 mM $IP_3$ was titrated with 100 mM NaOH. Similar concentrations were performed in the presence of Ca, Cd (12 mM) and Al, Fe (8 mM).

A strong metal complex will result in a lowering of pH at a certain amount NaOH added. The performed titrations show the relative metal binding properties. At pH 8 the binding properties are as follows: Ca<Cd<Fe<Al.

Example 9

Hydrolysis of sodium phytate with baker's yeast and fractionation of a mixture of inositol phosphates.

A 0.7 gram quantity of sodium phytate (from corn, Sigma Chemical Co) was dissolved in 600 ml sodium acetate buffer pH 4.6. 50 gram of baker's yeast from Jästbolaget, Sweden (dry substance: 28%, nitrogen content: 2%, phosphorus content: 0.4%) was added with stirring and incubation was continued at 45° C. The dephosphorylation was followed by determining the inorganic phosphorus released. After 7 hours when 50% inorganic phosphorus was liberated the hydrolysis was stopped by adding 30 ml of ammonia to pH 12. The suspension was centrifuged and the supernatant was collected.

400 ml of the supernatant was passed through an ion-exchange column (Dowex 1, chloride form, 25 mm × 250 mm) and eluted with a linear gradient of hydrochloric acid (0-0.7 N HCl).

Aliquots of eluted fractions were completely hydrolyzed in order to determine the contents of phosphorus and inositol. The peaks correspond to different inositol phosphates i.e. a peak with the ratio of phosphorus to inositol of three to one consists of inositol triphosphates etc.

Example 10

Structural determination of isomers of inositol triphosphate.

The fraction obtained in example 9 with a phosphorus/inositol ratio of three to one was neutralized and evaporated before analysis with H-NMR. Data show that the peak consists of myo-inositol-1,2,6-triphosphate.

Example 11

Solution of potassium salt of D-myo-inositol-1,2,6-triphosphate for injection.

0.5 g of the potassium salt of $IP_3$ and 0.77 g NaCl were dissolved in 98.73 ml of water for injection to form a solution suitable for injection into a person or an animal.

Example 12

Tablets of calcium salt of D-myo-inositol-1,2,6-triphosphate.

Tablets of the calcium salt of D-myo-inositol-1,2,6-triphosphate were produced in the following way. 50 g calcium salt of D-myo-inositol-1,2,6-triphospahte, 132 g lactose and 6 g acacia were mixed. Purified water was then added to the mixture, whereupon the mixing was continued until a suitable consistency was obtained. The mixture was sieved and dried. Then the mixture was blended with 10 g talcum and 2 g magnesium stearate. The mixture was compressed into tablets each weighing 200 mg.

Example 13

Two groups, each consisting of six rats, were fed a casein-based diet containing approximately 30% saturated fat. One group received D-myo-inositol-1,2,6-triphosphate ($IP_3$), 200 ppm, in the diet and the other group served as a control.

Platelet aggregation in response to thrombin was measured after two months.

The results were as follows:

| Treatment | Thrombin induced platelet aggregation (cm) | Number of animals |
|---|---|---|
| Control | 2.1 ± 0.9 | 6 |
| $IP_3$ | 0.5 ± 0.01 | 6 |

Thus, after two months of supplementation of IP$_3$ thrombin induced aggregation was significantly lower in the IP$_3$-treated animals compared to the controls.

Example 14

Thrombus formation induced by ADP in the microcirculation of the hamster cheek pouch was determined in the presence of D-myo-inositol-1,2,6-triphosphate (IP$_3$) compared to control.

The cheek pouch is everted in the anaesthetized animal and a micropipette containing ADP is placed close to a venule. ADP moves into the vessel and induces the formation of a thrombus on the wall of the venule. The growth rate of the thrombus is used to evaluate the effect of anti-thrombotic compounds.

IP$_3$, 5 mg/kg, was administered by infusion during a 10-minute period. Thrombus growth rates were determined at an interval of 5 minutes. Ten minutes after infusion 40% inhibition in growth rates was obtained, which shows IP$_3$ to be an efficient anti-thrombotic compound.

Example 15

Chronic administration of low oral doses of cadmium to rats induces moderate hypertension.

64 female rats (4 groups of 16 rats) were fed a rye-based Cd-free diet. The experiment was divided into two phases:

Phase 1: Induction of hypertension; groups 1 and 2 served as controls; groups 3 and 4 were given 0.1 ppM Cd in the drinking water. Phase 2: Reversal of Cd-induced hypertension; no group received Cd; groups 2 and 4 received 60 ppm D-myo-inositol-1,2,6-triphosphate (IP$_3$) in the drinking water.

The systolic blood pressure was measured by the tail cuff method at 4 week intervals throughout the experiment and the following results were obtained:

|  | Systolic blood pressure (mm Hg) | |
| --- | --- | --- |
|  | Phase 1 | Phase 2 |
| Group 1 | 120 | 120 |
| Group 2 | 119 | 125 |
| Group 3 | 136 | 138 |
| Group 4 | 133 | 124 |

The results show that Cd-induced hypertension can be reversed by adding IP$_3$ (group 4).

Example 16

Chronic administration of low oral doses of lead to rats induces moderate hypertension.

45 female rats (3 groups of 15 rats) were fed a rye-based Pb-free diet. The experiment was divided into two phases: Phase I: Induction of hypertension; group 1 served as control; groups 2 and 3 were given 1 ppm Pb in the drinking water. Phase 2: Reversal of Pb-induced hypertension; group 3 received 200 ppm D-myo-inositol-1,2,6-triphosphate (IP$_3$) in the diet.

The systolic blood pressure was measured by the tail cuff method at 4 weeks intevls throughout the experiment and the following results were obtained:

|  | Systolic blood pressure (mm Hg) | |
| --- | --- | --- |
|  | Phase 1 | Phase 2 |
| Group 1 | 122 | 120 |
| Group 2 | 133 | 134 |
| Group 3 | 132 | 121 |

The results show that Pb-induced hypertension can be reversed by adding IP$_3$ (group 3).

Example 17

Thirty male rats were fed a standard diet supplemented with 2% cholesterol and 1% cholic acid for a 14-day pretreatment period. During the subsequent 14-day treatment period one group of 10 rats was given the above diet with 0.2% D-myo-inositol-1,2,6-triphosphate (IP$_3$) added, while the other rats continued on the pretreatment diet and served as a control. The effect on serum concentration of lipid- and cholesterol metabolites is summarized below (%):

| Treatment | Total cholesterol | HDL cholesterol | Triglycerides | $\beta$-lipoprotein | Total lipids |
| --- | --- | --- | --- | --- | --- |
| Control | 100 | 100 | 100 | 100 | 100 |
| IP$_3$ | 78 | 116 | 98 | 82 | 95 |

Thus, it can be seen that the levels of cholesterol and $\beta$-lipoprotein is decreased, while the level of HDL-cholesterol is increased in the animals treated with IP$_3$. These data show that IP$_3$ has a beneficial effect on the lipids in the body.

Example 18

Fourteen rabbits were fed with a standard diet supplemented with 0.05% cholesterol and 18% butter. Six animals were also given 200 mg/kg D-myo-inositol-1,2,6-triphosphate (IP$_3$) added to the diet. The experiment was continued for 6 months. After this period the animals were killed and the severity of artherosclerosis in the aorta was determined. The results showed that in 4 out of 6 IP$_3$ treated animals, there were no lesions, while all 8 animals in the control group were artherosclerotic.

Thus, the occurence and severity of the artherosclerosis was dramatically reduced in the IP$_3$-treated animals.

Example 19

Injection of carrageenan into the subplanar surface of the rat hind-paw induces an inflammatory response that results in pronounced oedema. The degree of oedema can be reproducibly quantified by measuring paw circumference.

Two groups of five male rats were injected 2 hours and 1 hour before injection of carrageenan with 1000 mg/kg D-myo-inositol-1,2,6-triphosphate (IP$_3$) or Krebs ringer solution respectively.

Measurement of the paw diameter was made at hourly intervals.

The results show that an injection of IP$_3$ reduces the inflammation with 40% four hours after the induction of the inflammation. Thus, the inflammation in the IP$_3$-treated animals was strongly reduced.

Example 20

Transplant of an organ from one animal to another includes first a reduction of blood flow followed by reflow of blood in the new animal. During this process the organ is easily damaged and as a measurement the so called Schiff's base is determined.

In one group of six kidneys from rabbits the blood flow was first reduced for 120 minutes followed by reflow for 60 minutes. The other group of six kidneys was processed in the same way but two doses of 50 ppm D-myo-inositol-1,2,6-triphosphate (IP3) were administered 5 minutes before flow reduction and 5 minutes before reflow. Schiff's base was determined in cortex and medulla of the kidneys (% of control):

| Treatment | Schiff's base | |
|---|---|---|
| | Cortex | Medulla |
| Control | 100 | 100 |
| IP3 | 27 | 65 |

Thus, IP3-treated kidneys are strongly protected against damage during transplant.

Example 21

In an in vitro system consisting of cultured erythroleukemic cells (cell line K562) the ironchelating properties of D-myo-inositol-1,2,6-triphosphate (IP3) were studied.

The cells are preincubated with radio labelled iron.

The cells are immersed into an IP3-containing aqueous solution at a temperature of 37° C. The amount of iron released to the solution was measured. The results show that four times as much iron was released when IP3 was present in the solution. This shows that IP3 binds iron strongly.

Example 22

A 0.5 gram quantity of D-chiro-inositol was dissolved in 1 ml phosphoric acid at 60° C. 20 g polyphosphoric acid was added and the mixture was heated to 150° C. under vacuum for 6 hours. The mixture was diluted with water to a volume of 200 ml and passed through an ion-exchange column (Dowex 1, chloride form, 25 mm × 250 mm) and eluted with a linear gradient of hydrochloric acid (0–2.0 N HCl).

The content of the peak with the ratio of phosphorus to inositol of six to one was precipitated by addition of calciumhydroxide. The precipitate was filtered, washed and mixed with 10 ml of a cation-exchange resin to give the acid form of the inositolhexaphosphate. After neutralization with sodium hydroxide and freeze-drying the sodium salt of D-chiro-inositolhexaphosphate was obtained.

Example 23

A 0.8 gram quantity of epi-inositol was dissolved in 1.5 ml of phosphoric acid at 60° C. 32 g polyphosphoric acid was added and the mixture was heated to 150° C. under vacuum for 6 hours. The mixture was diluted with water to a volume of 200 ml and passed through an ion-exchange column (Dowex, chloride form, 25 mm × 250 mm) and eluted with a linear gradient of hydrochloric acid (0–2.0 N HCl).

The content of the peak with the ratio of phosphorus to inositol of six to one was precipitated by addition of calcium hydroxide. The precipitate was filtered, washed and mixed with 10 ml of a cation-exchange resin to give the acid form of the inositolhexaphosphate. After neutralization with sodium hydroxide and freeze-drying the sodium salt of epi-inositolhexaphosphate was obtained.

Example 24

A 0.8 gram quantity of the sodium salt of D-chiro-inositolhexaphosphate produced according to Example 22 was dissolved in 300 ml sodium acetate buffer, pH 5.2. 1.3 gram wheat phytase (EC 3.1.3.26, 0.015 U/mg from Sigma Chemical Co.) was added and the mixture was incubated at 38° C.

After the liberation of 50 % inorganic phosphorus the hydrolysis was stopped by adding ammonia to pH 12.

The mixture containing D-chiro-inositolphosphates was passed through an ion-exchange column (Dowex 1 chloride form, 25 mm × 250 mm) and eluted with a linear gradient of hydrochloric acid (0–0.7 N HCl).

The peak with the ratio of phosphorus to inositol of three to one was neutralized with 1.0M sodium hydroxide and freeze-dried.

Structural determination with NMR and IR showed the product to be D-chiro-inositoltriphosphate.

Example 25

A 1.2 gram quantity of the sodium salt of epi-inositolhexaphosphate produced according to Example 23 was dissolved in 500 ml sodium acetate buffer, pH 5.2. 2.0 gram wheat phytase (EC 3.1.3.26, 0.015 U/mg from Sigma Chemical Co.) was incubated at 38° C.

After the liberation of 50 % inorganic phosphorus the hydrolysis was stopped by adding ammonia to pH 12.

The mixture containing epi-inositolphosphates was passed through an ion-exchange column (Dowex 1, chloride form, 25 mm × 250 mm) and eluted with a linear gradient of hydrochloric acid (0–0.7 N HCl). The peak wit the ratio of phosphorus to inositol of three to one was neutralized with 1.0M sodium hydroxide and freeze-dried.

Structural determination with NMR and IR showed the product to be epi-inositoltriphosphate.

For purposes of further understanding the invention, formulas are given below of the IP3 isomers of the invention. Formulas are also given for IP6, IP5, IP4 and IP2.

The lower phosphate-esters of myoinositol are named depending on where the phosphoric acid groups are situated on the inositol ring, with the numbering giving as low position numbers as possible. L and D stand for clock-wise and counterclock-wise counting respectively, and are used depending on which result gives the lowest position number. The carbon atom which has an axial phosphoric acid group always has the position number 2. The structural formulas below are simplified to the acid form.

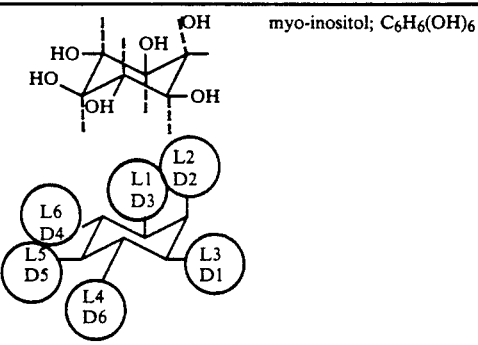

myo-inositol; $C_6H_6(OH)_6$

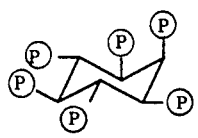 1,2,3,4,5,6-hexakis-(dihydrogen-phosphate)-myo-inositol alternatively myo-inositol hexakis (phosphate) or IP$_6$

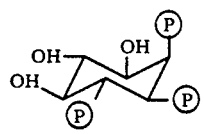 D-myo-inositol-1,2,6-triphosphate alternatively D-1,2,6-IP$_3$

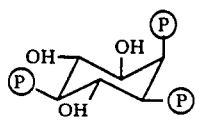 D-myo-inositol-1,2,5-triphosphate alternatively D-1,2,5-IP$_3$

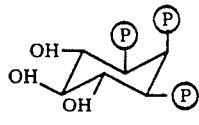 myo-inositol-1,2,3-triphosphate alternatively 1,2,3-IP$_3$

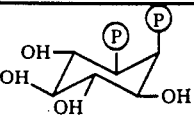 L-myo-inositol-1,2-diphosphate alternatively L-1,2-IP$_2$

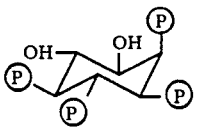 D-myo-inositol-1,2,5,6-tetra-phosphate or D-1,2,5,6-IP$_4$

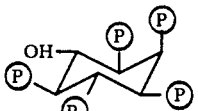 L-myo-inositol-1,2,3,4,5-penta phosphate or L-1,2,3,4,5-IP$_5$ $P = -O-PO_3H_2$

I claim:

1. A method of treating an inflammatory condition in a human or an animal comprising administering to a human or an animal in need thereof pharmaceutically effective amount of at least one isomer of an inositol triphosphate.

2. A method according to claim 1 wherein said inflammatory condition is arthritis.

* * * * *